(12) United States Patent
Schall

(10) Patent No.: US 8,535,311 B2
(45) Date of Patent: Sep. 17, 2013

(54) ELECTROSURGICAL INSTRUMENT COMPRISING CLOSING AND FIRING SYSTEMS

(75) Inventor: Christopher J. Schall, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 739 days.

(21) Appl. No.: 12/765,175

(22) Filed: Apr. 22, 2010

(65) Prior Publication Data

US 2011/0264093 A1 Oct. 27, 2011

(51) Int. Cl.
*A61B 18/14* (2006.01)

(52) U.S. Cl.
USPC .............................. 606/51; 606/52

(58) Field of Classification Search
USPC .................. 606/37, 39, 40, 51, 52, 206–208; 607/99
See application file for complete search history.

(56) References Cited

U.S. PATENT DOCUMENTS

| | | |
|---|---|---|
| 2,366,274 A | 1/1945 | Luth et al. |
| 2,458,152 A | 1/1949 | Eakins |
| 2,510,693 A | 6/1950 | Green |
| 3,166,971 A | 1/1965 | Stoecker |
| 3,580,841 A | 5/1971 | Cadotte et al. |
| 3,703,651 A | 11/1972 | Blowers |
| 4,005,714 A | 2/1977 | Hiltebrandt |
| 4,058,126 A | 11/1977 | Leveen |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,545,926 A | 10/1985 | Fouts, Jr. et al. |
| 4,582,236 A | 4/1986 | Hirose |
| 4,761,871 A | 8/1988 | O'Connor et al. |
| 4,849,133 A | 7/1989 | Yoshida et al. |
| 4,910,389 A | 3/1990 | Sherman et al. |
| 5,104,025 A | 4/1992 | Main et al. |
| 5,106,538 A | 4/1992 | Barma et al. |
| 5,108,383 A | 4/1992 | White |
| 5,190,541 A * | 3/1993 | Abele et al. .................... 606/46 |

(Continued)

FOREIGN PATENT DOCUMENTS

| | | |
|---|---|---|
| DE | 20004812 U1 | 9/2000 |
| DE | 10201569 A1 | 7/2003 |

(Continued)

OTHER PUBLICATIONS

International Search Report for PCT/US2011/031157, Oct. 12, 2011 (4 pages).

(Continued)

*Primary Examiner* — Michael Peffley
*Assistant Examiner* — Thomas Giuliani

(57) ABSTRACT

An electrosurgical surgical instrument can comprise a handle and an end effector, wherein the end effector can comprise first and second jaws which can be opened and closed to capture tissue therebetween. The handle can comprise a closure drive for closing the jaws and a firing drive which can be actuated independently of the closure drive. In various embodiments, a single trigger can be utilized to actuate both the closure drive and the firing drive, wherein a first range of motion of the trigger can actuate the closure drive and a second range of motion of the trigger can actuate the firing drive.

12 Claims, 7 Drawing Sheets

(56) References Cited

U.S. PATENT DOCUMENTS

| | | |
|---|---|---|
| 5,205,459 A | 4/1993 | Brinkerhoff et al. |
| 5,285,945 A | 2/1994 | Brinkerhoff et al. |
| 5,309,927 A | 5/1994 | Welch |
| 5,318,589 A | 6/1994 | Lichtman |
| 5,387,207 A | 2/1995 | Dyer et al. |
| 5,389,098 A | 2/1995 | Tsuruta et al. |
| 5,395,312 A | 3/1995 | Desai |
| 5,403,312 A | 4/1995 | Yates et al. |
| 5,428,504 A | 6/1995 | Bhatla |
| 5,496,317 A | 3/1996 | Goble et al. |
| 5,504,650 A | 4/1996 | Katsui et al. |
| 5,511,556 A | 4/1996 | DeSantis |
| 5,522,839 A | 6/1996 | Pilling |
| 5,558,671 A | 9/1996 | Yates |
| 5,563,179 A | 10/1996 | Stone et al. |
| 5,599,350 A | 2/1997 | Schulze et al. |
| 5,624,452 A | 4/1997 | Yates |
| 5,647,871 A | 7/1997 | Levine et al. |
| 5,665,085 A | 9/1997 | Nardella |
| 5,665,100 A | 9/1997 | Yoon |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,716,366 A | 2/1998 | Yates |
| 5,735,848 A | 4/1998 | Yates et al. |
| 5,752,973 A | 5/1998 | Kieturakis |
| 5,755,717 A | 5/1998 | Yates et al. |
| 5,762,255 A | 6/1998 | Chrisman et al. |
| 5,797,941 A | 8/1998 | Schulze et al. |
| 5,800,432 A | 9/1998 | Swanson |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,876,401 A | 3/1999 | Schulze et al. |
| 5,880,668 A | 3/1999 | Hall |
| 5,906,625 A | 5/1999 | Bito et al. |
| 5,984,938 A | 11/1999 | Yoon |
| 6,003,517 A | 12/1999 | Sheffield et al. |
| 6,013,052 A | 1/2000 | Durman et al. |
| 6,063,098 A | 5/2000 | Houser et al. |
| 6,068,629 A | 5/2000 | Haissaguerre et al. |
| 6,074,389 A | 6/2000 | Levine et al. |
| 6,099,483 A | 8/2000 | Palmer et al. |
| 6,099,550 A | 8/2000 | Yoon |
| H1904 H | 10/2000 | Yates et al. |
| 6,206,876 B1 | 3/2001 | Levine et al. |
| 6,292,700 B1 | 9/2001 | Morrison et al. |
| 6,340,878 B1 | 1/2002 | Oglesbee |
| H2037 H | 7/2002 | Yates et al. |
| 6,443,968 B1 | 9/2002 | Holthaus et al. |
| 6,464,702 B2 | 10/2002 | Schulze et al. |
| 6,500,176 B1 | 12/2002 | Truckai et al. |
| 6,503,248 B1 | 1/2003 | Levine |
| 6,514,252 B2 | 2/2003 | Nezhat et al. |
| 6,517,565 B1 | 2/2003 | Whitman et al. |
| 6,533,784 B2 | 3/2003 | Truckai et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,589,200 B1 | 7/2003 | Schwemberger et al. |
| 6,602,252 B2 | 8/2003 | Mollenauer |
| 6,635,057 B2 | 10/2003 | Harano et al. |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,789,939 B2 | 9/2004 | Schrödinger et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,066,936 B2 | 6/2006 | Ryan |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,101,372 B2 | 9/2006 | Dycus et al. |
| 7,112,201 B2 | 9/2006 | Truckai et al. |
| 7,125,409 B2 | 10/2006 | Truckai et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,235,073 B2 | 6/2007 | Levine et al. |
| 7,267,685 B2 | 9/2007 | Butaric et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,371,227 B2 | 5/2008 | Zeiner |
| 7,381,209 B2 | 6/2008 | Truckai et al. |
| 7,396,356 B2 | 7/2008 | Mollenauer |
| 7,404,508 B2 | 7/2008 | Smith et al. |
| 7,407,077 B2 | 8/2008 | Ortiz et al. |
| 7,435,582 B2 | 10/2008 | Zimmermann et al. |
| 7,445,621 B2 | 11/2008 | Dumbauld et al. |
| 7,464,846 B2 | 12/2008 | Shelton, IV et al. |
| 7,488,319 B2 | 2/2009 | Yates |
| 7,491,201 B2 | 2/2009 | Shields et al. |
| 7,510,107 B2 | 3/2009 | Timm et al. |
| 7,513,025 B2 | 4/2009 | Fischer |
| 7,517,349 B2 | 4/2009 | Truckai et al. |
| 7,550,216 B2 | 6/2009 | Ofer et al. |
| 7,559,452 B2 | 7/2009 | Wales et al. |
| 7,588,176 B2 | 9/2009 | Timm et al. |
| 7,597,693 B2 | 10/2009 | Garrison |
| 7,604,150 B2 | 10/2009 | Boudreaux |
| 7,628,792 B2 | 12/2009 | Guerra |
| 7,641,671 B2 | 1/2010 | Crainich |
| 7,644,848 B2 | 1/2010 | Swayze et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,607 B2 | 5/2010 | Dumbauld et al. |
| 7,753,904 B2 | 7/2010 | Shelton, IV et al. |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,803,156 B2 | 9/2010 | Eder et al. |
| 7,815,641 B2 | 10/2010 | Dodde et al. |
| 7,819,298 B2 | 10/2010 | Hall et al. |
| 7,832,408 B2 | 11/2010 | Shelton, IV et al. |
| 7,832,612 B2 | 11/2010 | Baxter, III et al. |
| 7,879,035 B2 | 2/2011 | Garrison et al. |
| 7,879,070 B2 | 2/2011 | Ortiz et al. |
| 7,931,649 B2 | 4/2011 | Couture et al. |
| 7,935,114 B2 | 5/2011 | Takashino et al. |

| | | |
|---|---|---|
| 7,955,331 B2 | 6/2011 | Truckai et al. |
| 7,963,963 B2 | 6/2011 | Francischelli et al. |
| 7,981,113 B2 | 7/2011 | Truckai et al. |
| 8,070,036 B1 | 12/2011 | Knodel et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,246,618 B2 | 8/2012 | Bucciaglia et al. |
| 8,298,232 B2 | 10/2012 | Unger |
| 2002/0165541 A1 | 11/2002 | Whitman |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0158548 A1 | 8/2003 | Phan et al. |
| 2003/0216722 A1 | 11/2003 | Swanson |
| 2004/0019350 A1 | 1/2004 | O'Brien et al. |
| 2004/0138621 A1 | 7/2004 | Jahns et al. |
| 2004/0193150 A1 | 9/2004 | Sharkey et al. |
| 2004/0232196 A1 | 11/2004 | Shelton, IV et al. |
| 2005/0085809 A1 | 4/2005 | Mucko et al. |
| 2005/0165429 A1 | 7/2005 | Douglas et al. |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0217709 A1 | 9/2006 | Couture et al. |
| 2007/0027469 A1 | 2/2007 | Smith et al. |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173813 A1 | 7/2007 | Odom |
| 2007/0191713 A1 | 8/2007 | Eichmann et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0239025 A1 | 10/2007 | Wiener et al. |
| 2007/0260242 A1 | 11/2007 | Dycus et al. |
| 2008/0071269 A1 | 3/2008 | Hilario et al. |
| 2008/0147062 A1 | 6/2008 | Truckai et al. |
| 2008/0167522 A1 | 7/2008 | Giordano et al. |
| 2008/0188851 A1 | 8/2008 | Truckai et al. |
| 2008/0221565 A1 | 9/2008 | Eder et al. |
| 2008/0262491 A1 | 10/2008 | Swoyer et al. |
| 2008/0294158 A1 | 11/2008 | Pappone et al. |
| 2008/0296345 A1* | 12/2008 | Shelton et al. ............ 227/176.1 |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125027 A1 | 5/2009 | Fischer |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0320268 A1 | 12/2009 | Cunningham et al. |
| 2010/0010299 A1 | 1/2010 | Bakos et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0036405 A1 | 2/2010 | Giordano et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0237132 A1 | 9/2010 | Measamer et al. |
| 2010/0264194 A1 | 10/2010 | Huang et al. |
| 2011/0087208 A1 | 4/2011 | Boudreaux et al. |
| 2011/0087209 A1 | 4/2011 | Boudreaux et al. |
| 2011/0087218 A1* | 4/2011 | Boudreaux et al. ............ 606/41 |
| 2011/0087219 A1 | 4/2011 | Boudreaux et al. |
| 2011/0087220 A1 | 4/2011 | Felder et al. |
| 2011/0155781 A1 | 6/2011 | Swensgard et al. |
| 2011/0238065 A1 | 9/2011 | Hunt et al. |
| 2011/0251608 A1 | 10/2011 | Timm et al. |
| 2011/0251609 A1 | 10/2011 | Johnson et al. |
| 2011/0251612 A1 | 10/2011 | Faller et al. |
| 2011/0251613 A1 | 10/2011 | Guerra et al. |
| 2011/0276057 A1 | 11/2011 | Conlon et al. |
| 2011/0282339 A1 | 11/2011 | Weizman et al. |
| 2011/0306963 A1 | 12/2011 | Dietz et al. |
| 2011/0306964 A1 | 12/2011 | Stulen et al. |
| 2011/0306965 A1 | 12/2011 | Norvell et al. |
| 2011/0306966 A1 | 12/2011 | Dietz et al. |
| 2011/0306967 A1 | 12/2011 | Payne et al. |
| 2011/0306968 A1 | 12/2011 | Beckman et al. |
| 2011/0306972 A1 | 12/2011 | Widenhouse et al. |
| 2011/0306973 A1 | 12/2011 | Cummings et al. |
| 2012/0010615 A1 | 1/2012 | Cummings et al. |
| 2012/0010616 A1 | 1/2012 | Huang et al. |
| 2012/0012636 A1 | 1/2012 | Beckman et al. |
| 2012/0012638 A1 | 1/2012 | Huang et al. |
| 2012/0016413 A1 | 1/2012 | Timm et al. |
| 2012/0022519 A1 | 1/2012 | Huang et al. |
| 2012/0022524 A1 | 1/2012 | Timm et al. |
| 2012/0022525 A1 | 1/2012 | Dietz et al. |
| 2012/0022526 A1 | 1/2012 | Aldridge et al. |
| 2012/0022527 A1 | 1/2012 | Woodruff et al. |
| 2012/0022528 A1 | 1/2012 | White et al. |
| 2012/0022529 A1 | 1/2012 | Shelton, IV et al. |
| 2012/0022530 A1 | 1/2012 | Woodruff et al. |
| 2012/0101488 A1 | 4/2012 | Aldridge et al. |
| 2012/0150176 A1 | 6/2012 | Weizman |
| 2013/0023875 A1 | 1/2013 | Harris et al. |
| 2013/0053831 A1 | 2/2013 | Johnson et al. |

FOREIGN PATENT DOCUMENTS

| | | |
|---|---|---|
| EP | 0630612 A1 | 12/1994 |
| EP | 0705571 A1 | 4/1996 |
| EP | 0640317 B1 | 9/1999 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| WO | WO 93/22973 A1 | 11/1993 |
| WO | WO 96/35382 A1 | 11/1996 |
| WO | WO 98/00069 A1 | 1/1998 |
| WO | WO 98/57588 A1 | 12/1998 |
| WO | WO 99/23960 A1 | 5/1999 |
| WO | WO 99/40861 A1 | 8/1999 |
| WO | WO 00/25691 A1 | 5/2000 |
| WO | WO 01/28444 A1 | 4/2001 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/059741 A1 | 5/2009 |
| WO | WO 2009/082477 A2 | 7/2009 |

| | | | |
|---|---|---|---|
| WO | WO 2010/017266 A1 | 2/2010 | |
| WO | WO 2010/104755 A1 | 9/2010 | |
| WO | WO 2011/089717 A1 | 7/2011 | |

OTHER PUBLICATIONS

U.S. Appl. No. 13/221,410, filed Aug. 30, 2011.
U.S. Appl. No. 13/189,169, filed Jul. 22, 2011.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, *Engineering Formulas* § Z.7 (7th ed. 1997).
U.S. Appl. No. 12/576,756, filed Oct. 9, 2009.
U.S. Appl. No. 12/576,776, filed Oct. 9, 2009.
U.S. Appl. No. 12/576,789, filed Oct. 9, 2009.
U.S. Appl. No. 12/576,808, filed Oct. 9, 2009.
U.S. Appl. No. 12/576,831, filed Oct. 9, 2009.
U.S. Appl. No. 12/836,366, filed Jul. 14, 2010.
U.S. Appl. No. 12/836,383, filed Jul. 14, 2010.
U.S. Appl. No. 12/836,396, filed Jul. 14, 2010.
U.S. Appl. No. 12/842,464, filed Jul. 23, 2010.
U.S. Appl. No. 12/842,476, filed Jul. 23, 2010.
U.S. Appl. No. 12/842,507, filed Jul. 23, 2010.
U.S. Appl. No. 12/842,518, filed Jul. 23, 2010.
U.S. Appl. No. 12/842,538, filed Jul. 23, 2010.
U.S. Appl. No. 12/842,565, filed Jul. 23, 2010.
U.S. Appl. No. 12/758,253, filed Apr. 12, 2010.
U.S. Appl. No. 12/758,268, filed Apr. 12, 2010.
U.S. Appl. No. 12/758,284, filed Apr. 12, 2010.
U.S. Appl. No. 12/758,298, filed Apr. 12, 2010.
U.S. Appl. No. 12/911,943, filed Oct. 26, 2010.
U.S. Appl. No. 12/841,480, filed Jul. 22, 2010.
U.S. Appl. No. 12/963,001, filed Dec. 8, 2010.
U.S. Appl. No. 12/732,992, filed Mar. 26, 2010.
U.S. Appl. No. 12/797,207, filed Jun. 9, 2010.
U.S. Appl. No. 12/797,252, filed Jun. 9, 2010.
U.S. Appl. No. 12/797,288, filed Jun. 9, 2010.
U.S. Appl. No. 12/797,305, filed Jun. 9, 2010.
U.S. Appl. No. 12/841,370, filed Jul. 22, 2010.
U.S. Appl. No. 12/797,844, filed Jun. 10, 2010.
U.S. Appl. No. 12/797,853, filed Jun. 10, 2010.
U.S. Appl. No. 12/797,861, filed Jun. 10, 2010.
U.S. Appl. No. 12/797,866, filed Jun. 10, 2010.
U.S. Appl. No. 12/832,345, filed Jul. 8, 2010.
U.S. Appl. No. 12/832,361, filed Jul. 8, 2010.
U.S. Appl. No. 12/781,243, filed May 17, 2010.
U.S. Appl. No. 12/775,724, filed May 7, 2010.
U.S. Appl. No. 12/622,113, filed Nov. 19, 2009.
U.S. Appl. No. 12/635,415, filed Dec. 10, 2009.
U.S. Appl. No. 12/647,134, filed Dec. 24, 2009.
Wright, et al., "Time-Temperature Equivalence of Heat-Induced Changes in Cells and Proteins," Feb. 1998. ASME Journal of Biomechanical Engineering, vol. 120, pp. 22-26.

* cited by examiner

ELECTROSURGICAL INSTRUMENT COMPRISING CLOSING AND FIRING SYSTEMS

BACKGROUND

1. Field of the Invention

The present invention relates to medical devices and methods. More particularly, the present invention relates to electrosurgical instruments and methods for sealing and transecting tissue.

2. Description of the Related Art

In various open, endoscopic, and/or laparoscopic surgeries, for example, it may be necessary to coagulate, seal, and/or fuse tissue. One means of sealing tissue relies upon the application of electrical energy to tissue captured within an end effector of a surgical instrument in order to cause thermal effects within the tissue. Various mono-polar and bi-polar radio frequency (Rf) surgical instruments and surgical techniques have been developed for such purposes. In general, the delivery of Rf energy to the captured tissue elevates the temperature of the tissue and, as a result, the energy can at least partially denature proteins within the tissue. Such proteins, such as collagen, for example, may be denatured into a proteinaceous amalgam that intermixes and fuses, or "welds", together as the proteins renature. As the treated region heals over time, this biological "weld" may be reabsorbed by the body's wound healing process.

In certain arrangements of a bi-polar radiofrequency (Rf) surgical instrument, the surgical instrument can comprise opposing first and second jaws, wherein the face of each jaw can comprise an electrode. In use, the tissue can be captured between the jaw faces such that electrical current can flow between the electrodes in the opposing jaws and through the tissue positioned therebetween. Such instruments may have to seal or "weld" many types of tissues, such as anatomic structures having walls with irregular or thick fibrous content, bundles of disparate anatomic structures, substantially thick anatomic structures, and/or tissues with thick fascia layers such as large diameter blood vessels, for example. With particular regard to sealing large diameter blood vessels, for example, such applications may require a high strength tissue weld immediately post-treatment.

The foregoing discussion is intended only to illustrate various aspects of the related art in the field of the invention at the time, and should not be taken as a disavowal of claim scope.

SUMMARY

In at least one form, a surgical instrument can comprise an end effector comprising a first jaw, a second jaw, wherein the first jaw is movable relative to the second jaw between an open position and a closed position, and at least one electrode. The surgical instrument can further comprise a closure member operably coupled with the first jaw, a firing member movable between a proximal position and a distal position, wherein the firing member comprises, one, a distal portion positionable within the end effector and, two, a proximal drive portion. The surgical instrument can further comprise a handle comprising a trigger rotatable between a first position, a second position, and a third position, and, in addition, a cam operably engaged with the trigger, wherein the trigger is configured to orient the cam in a first orientation when the trigger is in the first position and a second orientation when the trigger is in the second position. The cam can comprise a first cam portion operably engageable with the closure member, wherein the movement of the cam between the first orientation and the second orientation is configured to impart a closing motion to the closure member and move the first jaw between the open position and the closed position, and, in addition, a second cam portion operably engageable with the drive portion of the firing member, wherein the movement of the trigger between the second position and the third position is configured to impart a firing motion to the firing member and move the firing member from the proximal position to the distal position.

In at least one form, a surgical instrument can comprise an end effector comprising a first jaw, a second jaw, wherein the first jaw is movable relative to the second jaw between an open position and a closed position, and at least one electrode. The surgical instrument can further comprise a closure member operably coupled with the first jaw, and a firing member movable between a proximal position and a distal position, wherein the firing member comprises, one, a distal portion positionable within the end effector and, two, a proximal drive portion. The surgical instrument can further comprise a handle comprising a trigger movable through a first range of motion and a second range of motion, the trigger comprising a first cam portion operably engageable with the closure member, wherein the movement of the trigger through the first range of motion is configured to impart a closing motion to the closure member and move the first jaw between the open position and the closed position, and, in addition, a second cam portion operably engageable with the drive portion of the firing member, wherein the movement of the trigger through the second range of motion is configured to impart a firing motion to the firing member and move the firing member from the proximal position to the distal position.

In at least one form, a surgical instrument can comprise an end effector comprising a first jaw, a second jaw, wherein the first jaw is movable relative to the second jaw between an open position and a closed position, and at least one electrode. The surgical instrument can further comprise a closure member operably coupled with the first jaw and, in addition, a firing member movable between a proximal position and a distal position, wherein the firing member comprises, one, a distal portion positionable within the end effector and, two, a proximal drive portion. The surgical instrument can further comprise a handle comprising a trigger, wherein the handle comprises closing means for imparting a closing motion to the closure member and moving the first jaw between the open position and the closed position, and firing means for independently imparting a firing motion to the firing member and moving the firing member from the proximal position to the distal position after the closing means has applied the closing motion to the closure member, and wherein the firing motion and the closing motion are generated by a single stroke of the trigger.

The foregoing discussion should not be taken as a disavowal of claim scope.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
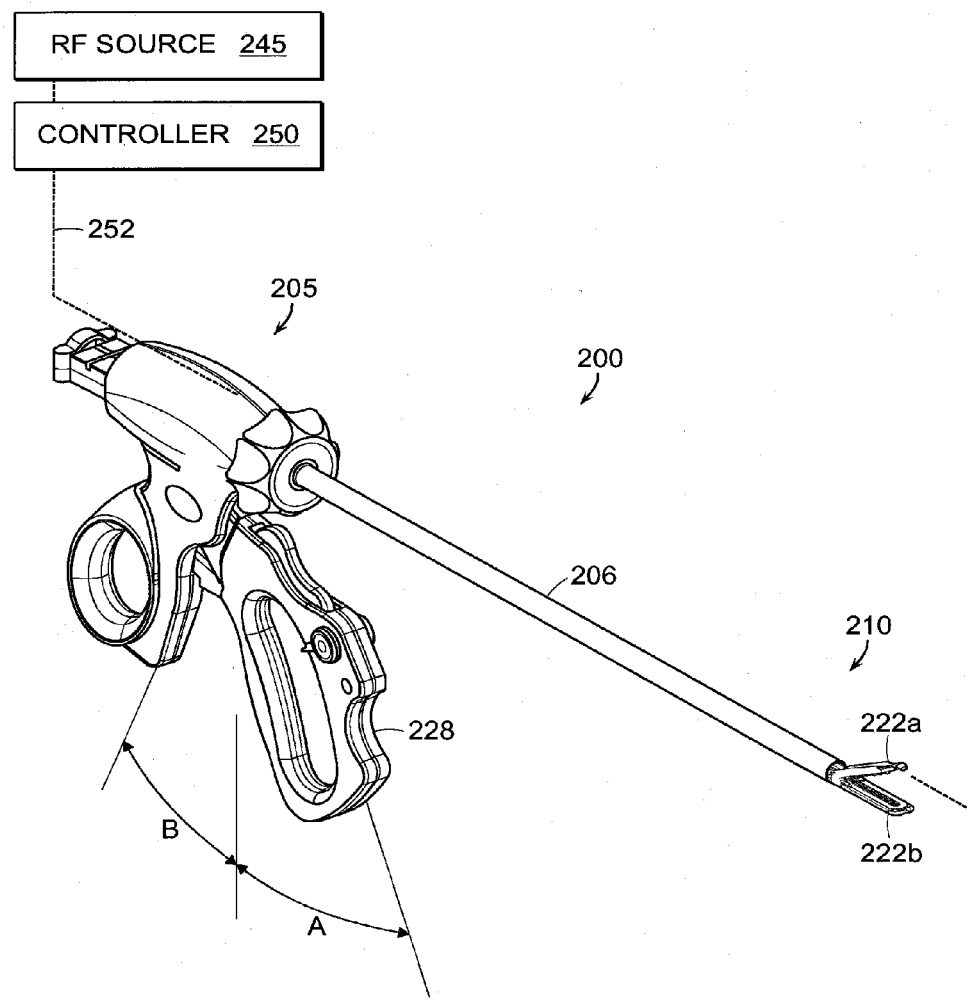
FIG. 1 is a perspective view of an electrosurgical instrument.

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

The entire disclosures of the following non-provisional United States patents are hereby incorporated by reference herein:

U.S. Pat. No. 7,381,209, entitled ELECTROSURGICAL INSTRUMENT;

U.S. Pat. No. 7,354,440, entitled ELECTROSURGICAL INSTRUMENT AND METHOD OF USE;

U.S. Pat. No. 7,311,709, entitled ELECTROSURGICAL INSTRUMENT AND METHOD OF USE;

U.S. Pat. No. 7,309,849, entitled POLYMER COMPOSITIONS EXHIBITING A PTC PROPERTY AND METHODS OF FABRICATION;

U.S. Pat. No. 7,220,951, entitled SURGICAL SEALING SURFACES AND METHODS OF USE;

U.S. Pat. No. 7,189,233, entitled ELECTROSURGICAL INSTRUMENT;

U.S. Pat. No. 7,186,253, entitled ELECTROSURGICAL JAW STRUCTURE FOR CONTROLLED ENERGY DELIVERY;

U.S. Pat. No. 7,169,146, entitled ELECTROSURGICAL PROBE AND METHOD OF USE;

U.S. Pat. No. 7,125,409, entitled ELECTROSURGICAL WORKING END FOR CONTROLLED ENERGY DELIVERY; and U.S. Pat. No. 7,112,201, entitled ELECTROSURGICAL INSTRUMENT AND METHOD OF USE.

Various embodiments of systems and methods of the invention relate to creating thermal "welds" or "fusion" within native tissue volumes. The alternative terms of tissue "welding" and tissue "fusion" may be used interchangeably herein to describe thermal treatments of a targeted tissue volume that result in a substantially uniform fused-together tissue mass, for example, in welding blood vessels that exhibit substantial burst strength immediately post-treatment. The strength of such welds is particularly useful for (i) permanently sealing blood vessels in vessel transection procedures; (ii) welding organ margins in resection procedures; (iii) welding other anatomic ducts wherein permanent closure is required; and also (iv) for performing vessel anastomosis, vessel closure or other procedures that join together anatomic structures or portions thereof. The welding or fusion of tissue as disclosed herein is to be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

At the molecular level, the phenomena of truly "welding" tissue as disclosed herein may result from the thermally-induced denaturation of collagen and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

Various embodiments disclosed herein provide electrosurgical jaw structures adapted for transecting captured tissue between the jaws and for contemporaneously welding the captured tissue margins with controlled application of RF energy. The jaw structures can comprise a scoring element which can cut or score tissue independently of the tissue capturing and welding functions of the jaw structures. The jaw structures can comprise first and second opposing jaws that carry positive temperature coefficient (PTC) bodies for modulating RF energy delivery to the engaged tissue.

Figure 2A:
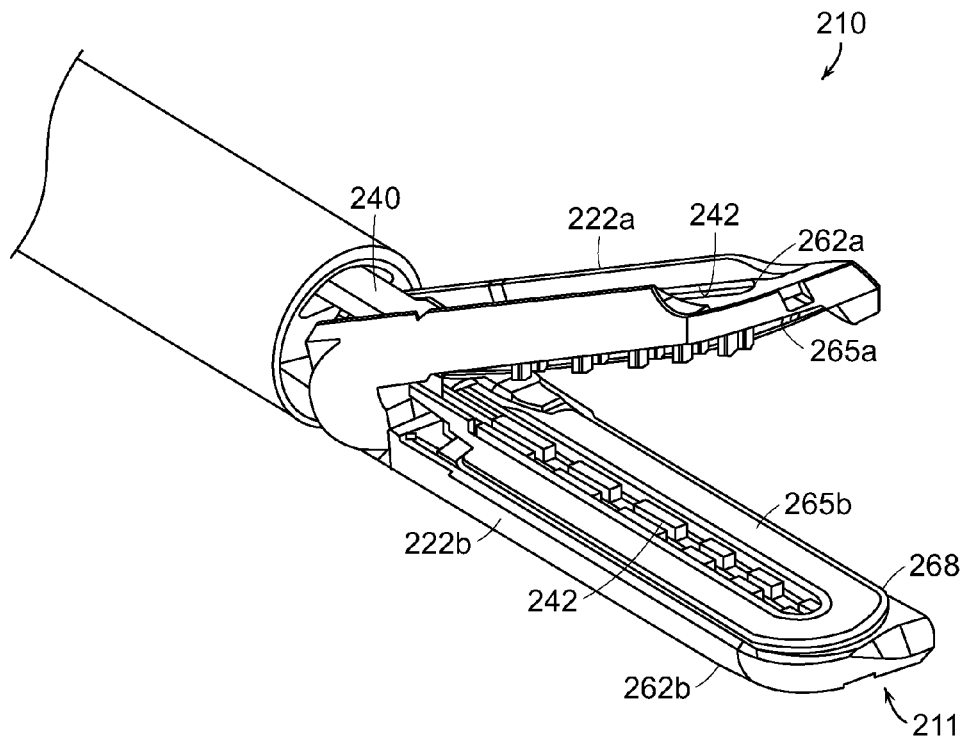
FIG. 2A illustrates an end effector of an electrosurgical instrument in an open configuration.
Figure 2B:
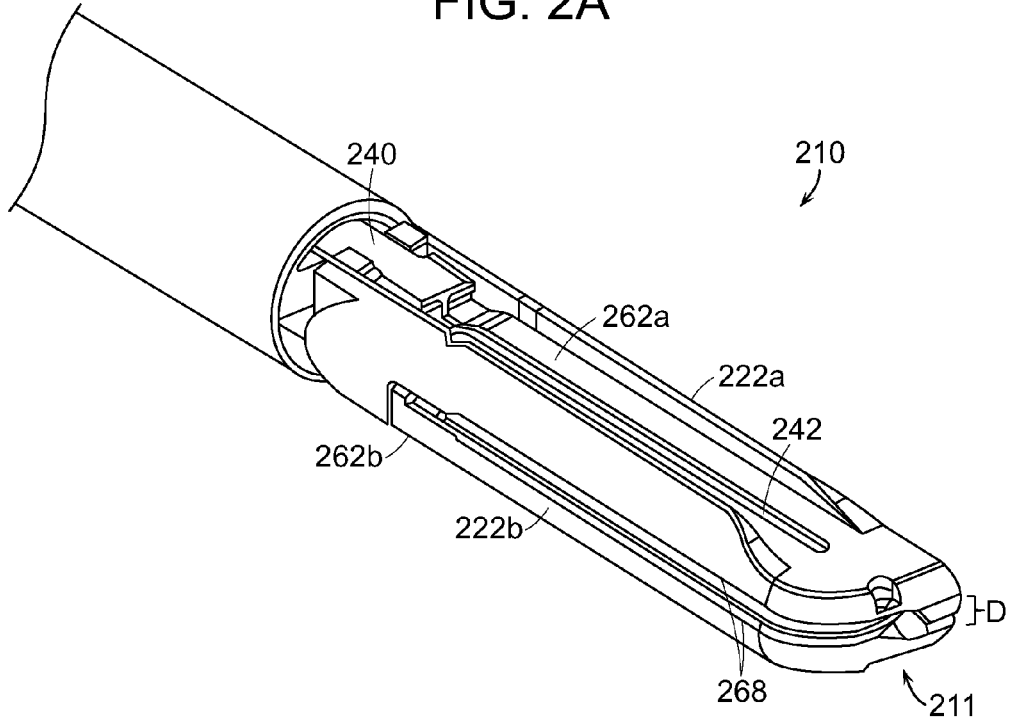
FIG. 2B illustrates the end effector of FIG. 2A in a closed configuration.

FIG. 1 illustrates an electrosurgical instrument 200 comprising a handle end 205, a shaft, or introducer, 206, and an end effector, or working end, 210. Shaft 206 can comprise any suitable cross-section, such as a cylindrical and/or rectangular cross-section, for example, and can comprise a tubular sleeve that extends from handle 205. End effector 210 can extend from shaft 206 and may be adapted for welding and transecting tissue. In various embodiments, end effector 210 can comprise an openable and closeable jaw assembly which can, in various embodiments, comprise straight, curved, and/ or any other suitably configured jaws. In various embodiments, the end effector 210 can comprise a first jaw 222a and a second jaw 222b, wherein at least one of the jaws 222a and 222b can move relative to the other. In at least one embodiment, the first jaw 222a can be pivoted about an axis relative to the second jaw 222b in order close onto, capture, and/or engage tissue positioned between the jaws and apply a compression force or pressure thereto. In various embodiments, the handle 205 can comprise a lever arm, or trigger, 228 adapted to actuate a translatable member 240. More particularly, in at least one embodiment, the lever arm 228 can be actuated in order to move member 240 distally toward the distal end 211 of end effector 210 and, when member 240 is advanced distally, member 240 can contact first jaw 222a and move it downwardly toward second jaw 222b, as illustrated in FIG. 2B. In at least one embodiment, the translatable member 240 can comprise a proximal rack portion and the lever arm 228 can comprise a plurality of gear teeth which can be configured to drive the proximal rack portion of translatable member 240 distally. In certain embodiments, rotation of the lever arm 228 in the opposite direction can drive the translatable member 240 proximally.

Figure 2C:
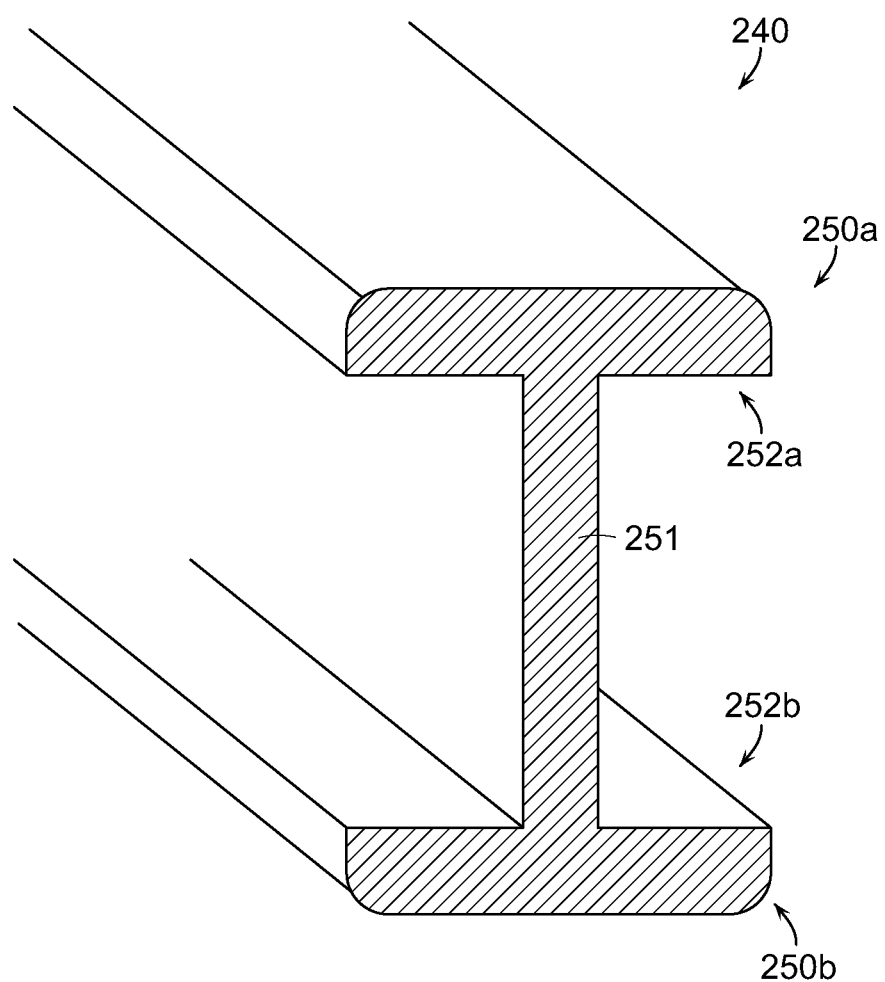
FIG. 2C is a sectional view of a translatable member shaped like an I-beam which is configured to close the end effector of the surgical instrument of FIG. 1.

As described above, the translatable member 240 can be configured to contact first jaw 222a and pivot jaw 222a toward second jaw 222b. In various embodiments, referring now to FIGS. 2A-2C, the distal end of reciprocating member 240 can comprise a flanged "I"-beam configured to slide within a channel 242 in the jaws 222a and 222b. Referring primarily to FIG. 2C, the I-beam portion of member 240 can comprise an upper flange 250a, a lower flange 250b, and a center, or intermediate, portion 251 connecting the flanges 250a and 250b. In at least one embodiment, the flanges 250a and 250b and the center portion 251 can define "c"-shaped channels on the opposite sides of member 240. In any event, in various embodiments, the flanges 250a and 250b can define inner cam surfaces 252a and 252b, respectively, for slidably engaging outward-facing surfaces 262a and 262b of jaws 222a and 222b, respectively. More particularly, the inner cam surface 252a can comprise a suitable profile configured to slidably engage the outer surface 262a of first jaw 222a and, similarly, the inner cam surface 252b can comprise a suitable profile configured to slidably engage the outer surface 262b of second jaw 222b such that, as translatable member 240 is advanced distally, the cam surfaces 252a and 252b can co-operate to cam first jaw member 222a toward second jaw member 222b and configure the end effector 240 in a closed configuration. As seen in FIG. 2B, jaws 222a and 222b can define a gap, or dimension, D between the first and second electrodes 265a and 265b of jaws 222a and 222b, respectively, when they are positioned in a closed configuration. In various embodiments, dimension D can equal a distance between approximately 0.0005" to approximately 0.005", for example, and, in at least one embodiment, between approximately 0.001" and approximately 0.002", for example.

As discussed above, the translatable member 240 can be at least partially advanced in order to move the first jaw 222a toward the second jaw 222b. Thereafter, the movable member 240 can be advanced further distally in order to transect the tissue positioned between the first jaw 222a and the second jaw 222b. In certain embodiments, the distal, or leading, end of the I-beam portion of 240 can comprise a sharp, or knife, edge which can be configured to incise the tissue. Before, during, and/or after the member 240 is advanced through the tissue, electrical current can be supplied to the electrodes in the first and second jaw members in order to weld the tissue, as described in greater detail further below. In various circumstances, the operation of the trigger 228 can advance the knife edge of the cutting member 240 to the very distal end of slot or channel 242. After the cutting member 240 has been sufficiently advanced, the trigger 288 can be released and moved into its original, or unactuated, position in order to retract the cutting member 240 and allow first jaw 222a to move into is open position again. In at least one such embodiment, the surgical instrument can comprise a jaw spring configured to bias the first jaw 222a into its open position and, in addition, a trigger spring configured to bias the trigger 228 into its unactuated position. Various other jaw closing mechanisms and electrosurgical energy-delivery surfaces are described in the following United States patents, the entire disclosures of which are incorporated herein by reference: U.S. Pat. Nos. 7,220,951; 7,189,233; 7,186,253; 7,125,409; 7,112,201; 7,087,054; 7,083,619; 7,070,597; 7,041,102; 7,011,657; 6,929,644; 6,926,716; 6,905,497; 6,802,843; 6,770,072; 6,656,177; 6,533,784; and 6,500,176.

In various embodiments, further to the above, the surgical instrument can comprise a first conductor, such as an insulated wire, for example, which can be operably coupled with the first electrode 265a in first jaw member 222a and, in addition, a second conductor, such as an insulated wire, for example, which can be operably coupled with the second electrode 265b in second jaw member 222b. In at least one embodiment, referring again to FIG. 1, the first and second conductors can extend through shaft 206 between an electrical connector in handle 205 and the electrodes 265a and 265b in the end effector 210. In use, the first and second conductors can be operably coupled to electrical source 245 and controller 250 by electrical leads in cable 252 in order for the electrodes 265a and 265b to function as paired bi-polar electrodes with a positive polarity (+) and a negative polarity (−). More particularly, in at least one embodiment, one of the first and second electrodes 265a and 265b can be operably coupled with a positive (+) voltage terminal of electrical source 245 and the other of the first and second electrodes 265a and 265b can be electrically coupled with the negative voltage (−) terminal of electrical source 245. Owing to the opposite polarities of electrodes 265a and 265b, current can flow through the tissue positioned between the electrodes 265a and 265b and heat the tissue to a desired temperature. In certain embodiments, the cutting member 240 can act as an electrode when it is electrically coupled to a positive terminal or negative terminal of the source 245, and/or any suitable ground.

As discussed above, the trigger 228 can be actuated in order to advance translatable member 240 distally, wherein the distal advancement of translatable member 240 can, one, close first jaw 222a and, two, transect tissue positioned between jaws 222a and 222b. In certain circumstances, the first jaw 222a may need to be moved into its fully closed position in order to apply a sufficient clamping pressure to the tissue as the tissue is welded and/or as the tissue is transected by the translatable member 240. In the above-described arrangement, however, the first jaw 222a may not be fully closed until the member 240 has been completely, or at least partially, advanced through the tissue. In circumstances where an insufficient clamping pressure is applied to the tissue, a less than desirable tissue weld may be created. Referring now to the embodiment illustrated in FIGS. 3-5, for example, an electrosurgical instrument 300 can comprise, one, a closure drive configured to close, or impart a closing motion to, the first jaw 322a of end effector 310 and, two, a separate, or independent, firing drive configured to advance, or impart a firing motion to, the translatable member 340 distally within the end effector 310. As described in greater detail below, the closure drive and the firing drive can be actuated by the same actuator, or trigger, such as trigger 328 of handle 305, for example.

In various embodiments, further to the above, the trigger 328 can be actuated in order to, first, actuate a closure drive to close first jaw 322a and, then, actuate a firing drive in order to advance translatable member 340 distally. Referring again to FIGS. 3-5, the trigger 328 can be movable between a first, unactuated position (FIG. 3), a second, partially-actuated position (FIG. 4), and a third, actuated position (FIG. 5). The trigger 328 can comprise a hand-grippable portion 329 which can be rotated, or pivoted, about a pivot pin 331 engaged with the handle housing 304 of handle 305 through a first range of motion, indicated by arrow A, between its first position (FIG. 3) and its second position (FIG. 4). The trigger 328 can further comprise a first cam portion, such as cam disk 330, for example, which can be configured to actuate the closure drive of instrument 300. In at least one embodiment, the cam disk 330 can be fixedly mounted to the trigger 328 such that the cam disk 330 rotates with the trigger 328. In various embodiments, the closure drive can comprise a closure link 350 and a closure member 352, wherein the rotation of trigger 328 between its first position and its second position can rotate cam disk 330 between a first orientation and a second orientation and, as a result of such rotation, pull closure link 350 and closure member 352 proximally. In at least one such embodiment, the closure link 350 can comprise a cam pin, or follower, 351 at one end thereof which can be positioned within a cam slot 333 in can disk 330 such that, owing to the contour of cam slot 333, the rotation of cam disk 330 can pull cam pin 351 proximally. More particularly, referring now to FIG. 6, the cam slot 333 can comprise a first portion, such as drive, or acceleration, portion 334, for example, which can be configured to drive the cam pin 351 between a first position 351a and a second position 351b when the trigger 328 is moved between its first and second positions in order to move cam pin 351 proximally, in a direction comprising a proximal component, and/or radially inwardly toward pivot pin 331. In at least one such embodiment, the cam slot 333 can be defined by a first sidewall 338 and an opposing second sidewall 339 wherein the first sidewall 338 can be configured to contact the cam pin 351 and move it from its first position 351a to its second position 351b as described above.

Owing to the movement of cam pin 351 between its first position 351a and its second position 351b, the entirety of closure link 350 can be moved proximally, or at least in a direction which comprises a proximal component. In various embodiments, referring again to FIG. 3, an opposite end of closure link 350 can comprise a guide pin 353 which can be positioned within a guide slot 306 in handle housing 304. When cam disk 330 is rotated between its first orientation (FIG. 3) and its second orientation (FIG. 4) as described above, the guide pin 353 can slide proximally within guide slot 306 in order to accommodate the movement of closure link 350 described above. In various embodiments, further to the above, an end of the closure member 352 can be connected to guide pin 353 such that, as guide pin 353 is slid proximally, the guide pin 353 can apply a pulling force to closure member 352 and move closure member 352 proximally. In at least one embodiment, the other end of closure member 352 can be connected to first jaw 322a such that, as closure member 352 is pulled proximally, the first jaw 322a can be rotated toward second jaw 322b about pivot 321, for example. As the first jaw 322a is moved into its closed position, as illustrated in FIG. 4, the first jaw 322a can compress the tissue positioned intermediate the first jaw 322a and the second jaw 322b. Further to the above, the first jaw 322a can be moved into its closed position before the translatable member 340 is advanced distally.

Figure 4:
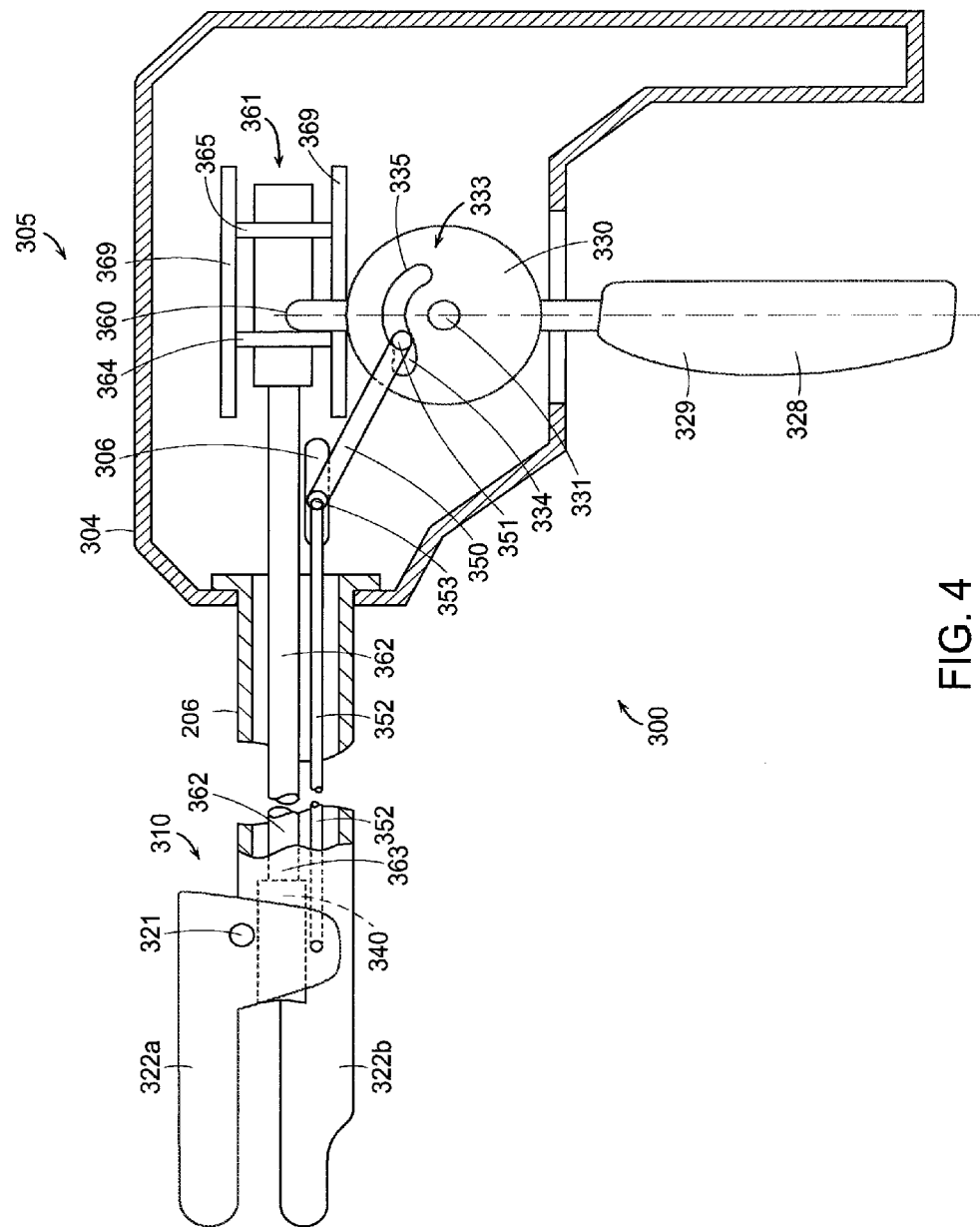
FIG. 4 is a cross-sectional view of the electrosurgical device of FIG. 3 illustrating the trigger after it has been moved through a first range of motion in order to retract a closure member and move the first jaw into a closed configuration.
Figure 5:
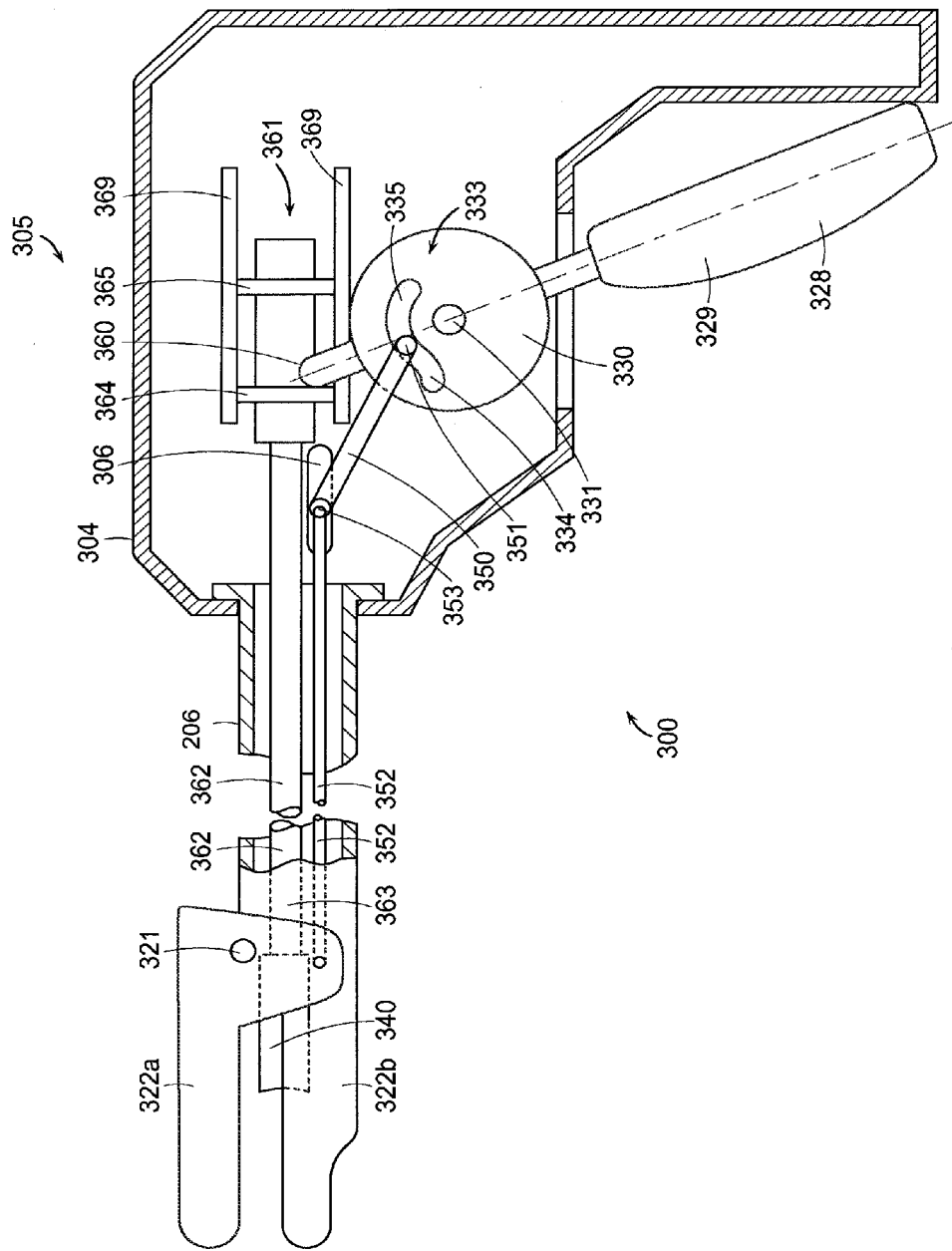
FIG. 5 is a cross-sectional view of the electrosurgical device of FIG. 3 illustrating the trigger after it has been moved through a second range of motion in order to advance a firing member and a cutting element operably engaged with the firing member.

Referring again to FIG. 3, the trigger 328 can further comprise a second cam portion, such as driver 360, for example, which can be configured to actuate the firing drive system. In various embodiments, the firing drive system can comprise a firing member 362 which can comprise a proximal end 361 and a distal end 363, wherein the driver 360 can be configured to operably engage the proximal end 361 in order to advance the firing member 362 distally, i.e., in a direction indicated by arrow D, for example. More particularly, in at least one embodiment, the proximal end 361 can comprise yoke including a distal drive surface 364 which can be engaged by the driver 360 as the trigger 328 is rotated through its second range of motion, indicated by arrow B, from its second position (FIG. 4) to its third position (FIG. 5). When firing member 362 is advanced distally, referring to FIG. 5, the firing member 362 can move cutting member 340 distally within the end effector 310. The reader will note that the driver 360 may not be operably engaged with distal drive surface 364, and/or any other portion of the proximal end 361 of firing member 362, throughout the first range of motion A of trigger 328 as trigger 328 is moved between its first, unactuated position (FIG. 3) and its second position (FIG. 4). In such embodiments, the trigger 328 may be utilized to close the first jaw 322a without advancing the firing member 362, at least until the first jaw 322a has been moved into its fully closed position. When the trigger 328 is in its second position, in at least one such embodiment, the driver 360 can be positioned against, or adjacent to, the distal drive surface 364. The trigger 328 may then be further rotated such that driver 360 applies a firing force to the distal drive surface 364 and advances the firing member 362 distally.

Figure 6:
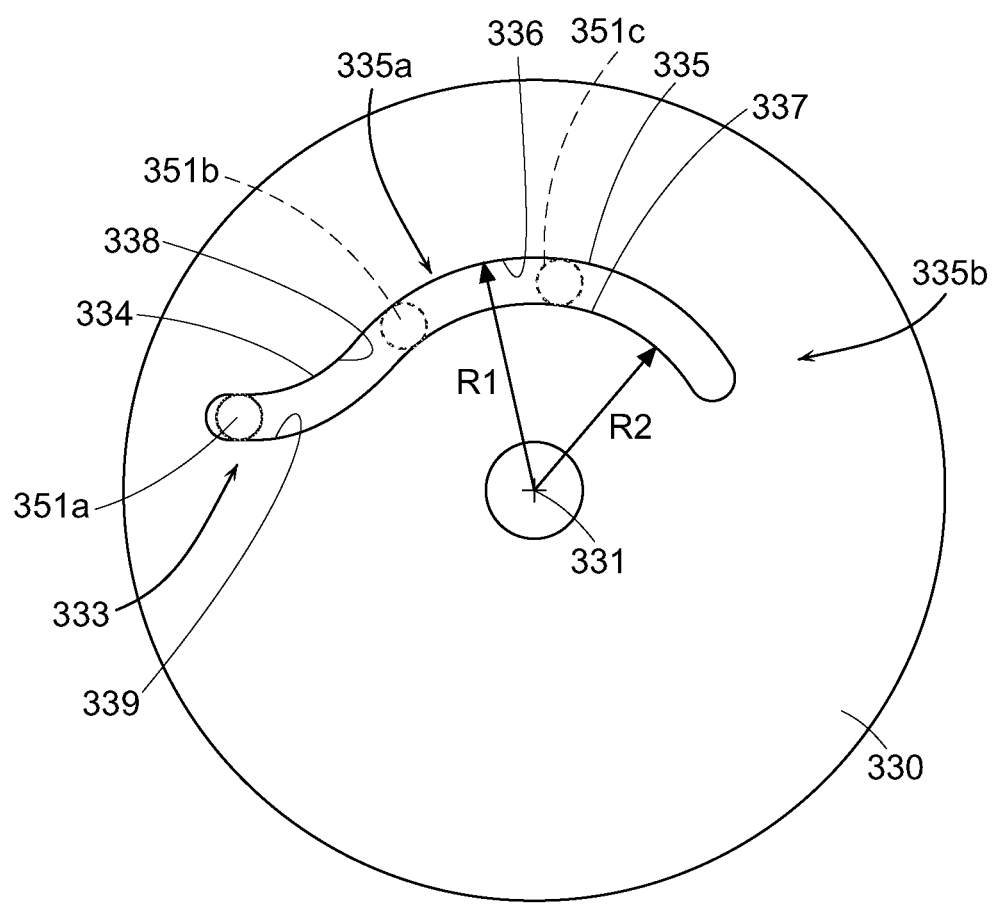
FIG. 6 is a detail view of a cam disk which is operably coupled to the trigger of FIG. 3, wherein the cam disk comprises a cam slot configured to receive a cam follower operably coupled to the closure member of FIG. 4.

In various embodiments, further to the above, the cam slot 333 of cam disk 330 can comprise a second portion, such as dwell portion 335, for example, which can be configured to receive cam pin 351 of closure link 350 after the cam pin 351 has passed through the first portion 334. In at least one such embodiment, dwell portion 335 can be defined by a constant, or at least substantially constant, radius of curvature which is concentric, or at least substantially concentric, about a rotation axis defined by pivot pin 331. In such embodiments, the cam disc 330 can move relative to the cam pin 351 when the trigger 328 is rotated from its second position to its third position without actuating the closure drive. More particularly, the cam pin 351 can ride within cam slot 333 as cam disk 330 is rotated between its second orientation (FIG. 4) and a third orientation (FIG. 5) without pushing and/or pulling the closure link 350 and the closure member 352. Such relative movement between cam pin 351 and cam slot 333 is represented in FIG. 6 which illustrates the second position of cam pin 351, i.e. position 351b, which corresponds to the second orientation of cam disk 330, and a third position of cam pin 351, i.e. position 351c, which corresponds to the third orientation of cam disk 330. As a result of the above, the first jaw 322a can be held in its closed position as the trigger 328 is moved through its second range of motion B from its second position (FIG. 4) and its third position (FIG. 5).

Figure 3:
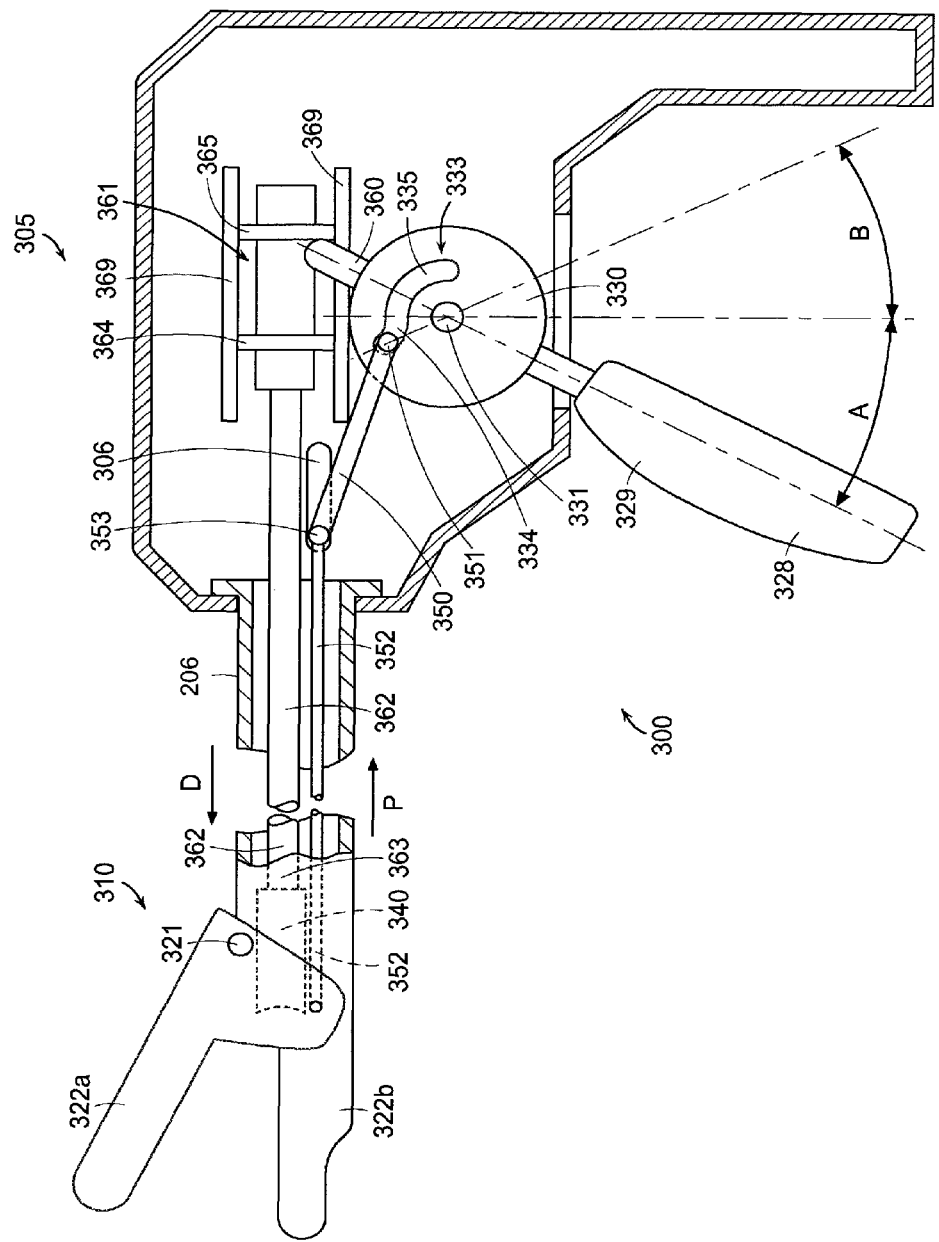
FIG. 3 is a cross-sectional view of an electrosurgical device comprising a trigger in an unactuated position and, in addition, an end effector comprising first and second jaws, wherein the first jaw is illustrated in an open configuration.

In various embodiments, as illustrated in FIG. 3, the handle housing 304 can comprise a channel and/or aperture, for example, which can be configured to receive and/or guide the proximal end 361 of firing member 362. In at least one embodiment, the channel can comprise guide members 369 positioned on opposite sides of proximal portion 361 which can be sized and configured such that little, if any, relative movement exists between the distal drive surface 364 and the guide members 369, for example. In various embodiments, the proximal end 361 of firing member 362 can further comprise a proximal drive surface, such as drive surface 365, for example, wherein the proximal drive surface 365 can be part of the yoke including distal drive surface 364. In various embodiments, similar to the above, the proximal drive surface 365 can be configured to be closely received between the guide members 369 such that little, if any, relative movement exists between the drive surface 365 and the guide members 369. In use, the proximal drive surface 365 can be utilized to retract the firing member 362 proximally, i.e., the direction indicated by arrow P. More particularly, the trigger 328 can be rotated back toward its second position and, as a result of such rotation, the driver 360 can come into contact with the proximal drive surface 365 and push the firing member 362 and the translatable member 340 proximally.

As the trigger 328 is rotated back into its second position, further to the above, the cam disk 330 can rotate relative to the cam pin 331 such that, owing to the constant, or at least substantially constant radius of curvature of dwell portion 335, the closure drive and first jaw 332a can remain in a closed configuration until the trigger 328 is rotated past its second position. Once the trigger 328 has passed through its second position (FIG. 4), the translatable member 340 and the firing member 362 may be in their unactuated, or unfired, positions and, in addition, the cam pin 351 may enter into the acceleration, or drive, portion 334 of cam slot 333. In such circumstances, the sidewall 339 of cam slot 333 may engage cam pin 351 and push cam pin 351 distally as the cam disk 330 is rotated into its first orientation and the trigger 328 is moved into its first position. When cam pin 351 is pushed distally, as described above, the closure link 350 can be pushed distally such that the guide pin 353 can slide distally within guide slot 306 and, as a result, push closure member 352 distally as well. Owing to the distal movement of closure member 352, the closure member 352 can rotate first jaw 322a about pivot 321, for example, into an open configuration, as illustrated in FIG. 3. In various embodiments, the surgical instrument 300 can comprise one or more springs or biasing members which can be configured to return trigger 328 into its first position and/or return first jaw 322a into its open configuration. In at least one such embodiment, the surgical instrument 300 can comprise a trigger spring operably coupled with the trigger 328 and the handle frame 304 such that, after the trigger 328 has been actuated, the trigger 328 can be released thereby allowing the trigger spring to return the trigger 328 to its first position, for example. In certain embodiments, the end effector 310 can further comprise a spring positioned intermediate the first jaw 332a and the second jaw 322b such that the spring can bias the first jaw 332a into its open configuration when the trigger 328 is released, for example.

As described above, referring again to FIG. 6, the dwell portion 335 of cam slot 333 can be defined by a constant, or at least substantially constant, radius of curvature. More particularly, in at least one embodiment, the dwell portion 335 can comprise, one, a first sidewall 336 which can be defined by a constant, or at least substantially constant, first radius of curvature R1 and, two, a second, opposing sidewall 337 which can be defined by a second constant, or at least substantially constant, radius of curvature R2. In various embodiments, the sidewalls 336 and 337 can be sufficiently spaced apart such that there is sliding contact between cam pin 351 and at least one of the sidewalls 336, 337. In at least one embodiment, the sidewalls 336 and 337 can define a width therebetween which is wider than the diameter of cam pin 351. Owing to the constant, or at least substantially constant, radius of curvature of dwell portion 335, the cam disk 330 may rotate relative to the cam pin 351 without driving the cam pin 351 proximally and/or distally, as described above. In certain alternative embodiments, the second portion 335 of cam slot 333 may have a non-constant radius of curvature. For example, the entrance portion 335a to second portion 335 may have a smaller radius of curvature than the end portion 335b of second portion 335 wherein, as a result, the second portion 335 may drive cam pin 351 distally during the second range of movement B of trigger 328. In embodiments where the first jaw 322a has already been positioned in its closed position by the first portion 334 of cam slot 333, the change in radius of the second portion 335 can apply additional clamping pressure to the tissue between the jaws 322a and 322b. In at least one such embodiment, the second portion 335 of cam slot 333 can apply a gradually increasing pressure to the tissue as the translatable member 340 is advanced within the end effector. In various embodiments, the increase in clamping pressure can be linear while, in certain embodiments, the increase in clamping pressure can be geometric, for example.

As discussed above, the surgical instrument 300 can comprise a rotatable trigger 328 which can be configured to actuate the closing drive and the firing drive of the surgical instrument 300 independently of one another. Other suitable triggers, such as linearly displaceable triggers, for example, are envisioned. In various embodiments, the surgical instrument 300 can comprise a switch which can be actuated in order to supply current to the electrodes positioned within the end effector 328. In certain embodiments, the surgical instrument 300 can further comprise a switch which can be tripped in order to supply current to the electrodes positioned within the end effector 310 when the trigger 328 is moved into its second position, for example. In at least one such embodiment, the switch can be in an open configuration as the trigger 328 is moved through its first range of motion A and, once tripped by trigger 328, the switch can be in a closed configuration as the trigger 328 is moved through its second range of motion B. In such embodiments, current may not flow through the electrodes in the end effector 310 as the trigger 328 is moved through its first range of motion A and as the first jaw 322a is being moved into its closed position. On the other hand, in such embodiments, current may flow through the electrodes as the trigger 328 is moved through its second range of motion B and as the cutting member 340 is being advanced distally by the trigger 328 as described above. In various embodiments, the switch can be positioned within handle 305 such that the switch is aligned with the trigger 328 when the trigger 328 is in its second position. In certain embodiments, the surgical instrument 300 can further comprise a second switch which can be switched from a closed configuration into an open configuration when the trigger 328 is moved into a fully actuated position, and/or its third position, for example. In at least one such embodiment the first switch and the second switch can be in series with one another such that both switches must be in a closed configuration in order for current to flow to the electrodes. In various embodiments, as a result, the actuation of the first switch can turn on the electrode current and the actuation of the second switch can turn off the electrode current, for example.

The surgical instruments 200, 300, and the system comprising electrical source 245 and controller 250, for example, may be configured to provide different electrosurgical energy-delivery operating modes which, in certain embodiments, may depend on the amount, or degree, of jaw closure. In any event, in various circumstances, further to the above, the degree of jaw closure may be represented by the degree of actuation of triggers 228, 328 such as, for example, degrees of actuation A and B illustrated in FIG. 1. Alternatively, the degree of actuation may be represented by the axial translation of reciprocating members 240, 340. In various circumstances, it may be useful to switch between different electrosurgical energy-delivery operating modes depending on the volume of tissue captured within the end effector of the surgical instrument and the amount of compression applied to the tissue. For example, the instruments 200, 300 may deliver Rf energy in a first operating mode to large volumes of the captured tissue in order to cause an initial dehydration of the tissue, wherein the surgical instruments 200, 300 may thereafter switch, and/or be switched by controller 250, for example, to a second operating mode which allows for more effective tissue welding. In various circumstances, this second operating mode may provide a greater amount or a lesser amount of energy to the tissue and/or adjust the manner or location in which the energy is being supplied to the tissue. Alternatively, when engaging a lesser volume of tissue, for example, the surgical instruments 200, 300 and/or accompanying system may deliver Rf energy in only one operating mode which can be best suited for tissue welding, for example.

In various embodiments, further to the above, a control system and/or controller 250 can switch the surgical instrument from one operating mode to another mode after the jaw has been closed a predetermined amount, wherein, in at least one embodiment the switchover can occur at 10%, 20%, 30%, 40%, 50%, 60%, 70%, and/or 80% of the jaw closure, for example. In certain embodiments, the surgical instrument can comprise a sensor configured to detect the degree to which first jaws 222a, 322a have been closed. In various embodiments, the switching between electrosurgical modes can be triggered by one or more operational parameters, such as (i) the degree of jaw closure as described above, (ii) the impedance of the engaged tissue, and/or (iii) the rate of change of impedance or any combination thereof. Furthermore, the polarity of the electrodes can be switched more than two times during the operation of the surgical instrument. Other operating modes are disclosed in U.S. patent application Ser. No. 12/050,462, entitled ELECTROSURGICAL INSTRUMENT AND METHOD, filed on Mar. 18, 2008, the entire disclosure of which is incorporated by reference herein.

In various embodiments, as described above, current can flow from one electrode to another while passing through the tissue captured by the end effector of the surgical instrument. As also described above, the current passing through the tissue can heat the tissue. In various circumstances, however, the tissue may become overheated. In order to avoid such overheating, the electrodes of various surgical instruments can comprise materials which may no longer conduct current, or may conduct at least substantially less current, when the electrode materials have reached or exceeded a certain temperature. Stated another way, in at least one embodiment, the electrical resistance of the electrode material can increase with the temperature of the material and, in certain embodiments, the electrical resistance of the material can increase significantly when the material has reached or exceeded a certain transition, or switching, temperature. In various circumstances, such materials can be referred to as positive temperature coefficient, or PTC, materials. In at least some such PTC materials, the PTC material can be comprised of a first non-conductive material, or substrate, which has a high electrical resistance and, in addition, a second, conductive material, or particles, having a lower electrical resistance interdispersed throughout the substrate material. In at least one embodiment, the substrate material can comprise polyethylene and/or high-density polyethylene (HDPE), for example, and the conductive material can comprise carbon particles, for example. In any event, when the temperature of the PTC material is below its transition temperature, the conductive material can be present in the non-conductive material in a sufficient volumetric density such that the current can flow through the PTC material via the conductive particles. When the temperature of the PTC material has exceeded its transition temperature, the substrate, or non-conductive material may have sufficiently expanded and/or changed states such that the conductive particles are no longer sufficiently in contact with one another in order provide a sufficient path for the current to flow therethrough. Stated another way, the expansion and/or state change of the substrate material may cause the volumetric density of the conductive particles to fall below a sufficient volumetric density in order for current to be conducted therethrough, or at least substantially conducted therethrough. In various circumstances, as a result of the above, the PTC material may act as a circuit breaker which can prevent, or at least inhibit, additional energy from reaching the tissue being treated, that is, at least until the PTC material has cooled sufficiently and reached a temperature which is below the transition, or switching, temperature. At such point, the PTC material could begin to conduct current again.

Further to the above, describing a material as having a positive temperature coefficient of resistance (PTC) can mean that the resistance of the material increases as the temperature of the material increases. Many metal-like materials exhibit electrical conduction that has a slight positive temperature coefficient of resistance. In such metal-like materials, the PTC's variable resistance effect is characterized by a gradual increase in resistance that is linearly proportional to temperature—that is, a linear PTC effect. A "nonlinear" PTC effect can be exhibited by certain types of polymer matrices, or substrates, that are doped with conductive particles. These polymer PTC compositions can comprise a base polymer that undergoes a phase change or can comprise a glass transition temperature Tg such that the PTC composition has a resistance that increases sharply over a narrow temperature range.

Polymeric PTC material can consist of a crystalline or semi-crystalline polymer (e.g., polyethylene) that carries a dispersed filler of conductive particles, such as carbon powder or nickel particles, for example, therein. In use, a polymeric PTC material can exhibit temperature-induced changes in the base polymer in order to alter the electrical resistance of the polymer-particle composite. In a low temperature state, the crystalline structure of the base polymer can cause dense packing of the conductive particles (i.e., carbon) into its crystalline boundaries so that the particles are in close proximity and allow current to flow through the PTC material via these carbon "chains". When the PTC material is at a low temperature, numerous carbon chains form the conductive paths through the material. When the PTC material is heated to a selected level, or an over-current causes I²R heating (Joule heating) within the PTC material, the polymer base material may be elevated in temperature until it exceeds a phase transformation temperature. As the polymer passes through this phase transformation temperature, the crystalline structure can change to an amorphous state. The amorphous state can cause the conductive particles to move apart from each other until the carbon chains are disrupted and can no longer conduct current. Thus, the resistance of the PTC material increases sharply. In general, the temperature at which the base polymer transitions to its amorphous state and affects conductivity is called its switching temperature Ts. In at least one embodiment, the transition or switching temperature Ts can be approximately 120 degrees Celsius, for example. In any event, as long as the base polymer of the PTC material stays above its switching temperature Ts, whether from external heating or from an overcurrent, the high resistance state will remain. Reversing the phase transformation allows the conductive particle chains to reform as the polymer re-crystallizes to thereby restore multiple current paths, and a low resistance, through the PTC material. Conductive polymer PTC compositions and their use are disclosed in U.S. Pat. Nos. 4,237,441; 4,304,987; 4,545,926; 4,849,133; 4,910,389; 5,106,538; and 5,880,668, the entire disclosures of which are incorporated by reference herein.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
    an end effector, comprising:
        a first jaw;
        a second jaw, wherein said first jaw is movable relative to said second jaw between an open position and a closed position; and
        at least one electrode;
    a closure member operably coupled with said first jaw;
    a firing member movable between a proximal position and a distal position, wherein said firing member comprises:
        a distal portion positionable within said end effector; and
        a proximal drive portion; and
    a handle, comprising:
        a trigger rotatable between a first position, a second position, and a third position;
        a cam operably engaged with said trigger, wherein said trigger is configured to orient said cam in a first orientation when said trigger is in said first position and a second orientation when said trigger is in said second position, and wherein said cam comprises:
            a first cam portion operably engageable with said closure member, wherein the movement of said cam between said first orientation and said second orientation is configured to impart a closing motion to said closure member and move said first jaw between said open position and said closed position; and
            a second cam portion operably engageable with said proximal drive portion of said firing member, wherein the movement of said trigger between said second position and said third position is configured to impart a firing motion to said firing member and move said firing member from said proximal position to said distal position, and wherein said cam is mounted to said trigger such that said cam is rotated with said trigger, wherein said first cam portion comprises a cam slot, wherein said closure member comprises a cam follower positioned within said cam slot, wherein said proximal drive portion comprises a proximal drive surface and a distal drive surface, and wherein said second cam portion comprises a drive member configured to engage said distal drive surface and move said firing member from said proximal position to said distal position when said trigger is moved from said second position to said third position.

2. The surgical instrument of claim 1, wherein said drive member is configured to engage said proximal drive surface of said drive portion when said trigger is moved from said third position to said second position.

3. The surgical instrument of claim 1, wherein said drive member is not engaged with said distal drive surface when said trigger is in said first position.

4. The surgical instrument of claim 1, wherein said cam slot comprises an acceleration portion corresponding to the rotation of said cam between said first orientation and said second orientation and a dwell portion corresponding to the rotation of said cam between said second orientation and a subsequent orientation of said cam.

5. The surgical instrument of claim 4, wherein said cam follower is configured to enter said dwell portion when said drive member is engaged with distal drive surface.

6. A surgical instrument, comprising:
an end effector, comprising:
   a first jaw;
   a second jaw, wherein said first jaw is movable relative to said second jaw between an open position and a closed position; and
   at least one electrode;
a closure member operably coupled with said first jaw;
a firing member movable between a proximal position and a distal position, wherein said firing member comprises:
   a distal portion positionable within said end effector; and
   a proximal drive portion; and
a handle, comprising:
   a trigger rotatable between a first position, a second position, and a third position;
   a cam operably engaged with said trigger, wherein said trigger is configured to orient said cam in a first orientation when said trigger is in said first position and a second orientation when said trigger is in said second position, and wherein said cam comprises:
     a first cam portion operably engageable with said closure member, wherein the movement of said cam between said first orientation and said second orientation is configured to impart a closing motion to said closure member and move said first jaw between said open position and said closed position; and
     a second cam portion operably engageable with said proximal drive portion of said firing member, wherein the movement of said trigger between said second position and said third position is configured to impart a firing motion to said firing member and move said firing member from said proximal position to said distal position, and wherein said closing motion is configured to pull said closure member proximally in order to close said first jaw, and wherein said firing motion is configured to push said firing member distally in order to advance said firing member within said end effector.

7. A surgical instrument, comprising:
an end effector, comprising:
   a first jaw;
   a second jaw, wherein said first jaw is movable relative to said second jaw between an open position and a closed position; and
   at least one electrode;
a closure member operably coupled with said first jaw;
a firing member movable between a proximal position and a distal position, wherein said firing member comprises:
   a distal portion positionable within said end effector; and
   a proximal drive portion; and
a handle comprising a trigger movable through a first range of motion and a second range of motion, said trigger comprising:
   a first cam portion operably engageable with said closure member, wherein the movement of said trigger through said first range of motion is configured to impart a closing motion to said closure member and move said first jaw between said open position and said closed position; and
   a second cam portion operably engageable with said proximal drive portion of said firing member, wherein the movement of said trigger through said second range of motion is configured to impart a firing motion to said firing member and move said firing member from said proximal position to said distal position, and wherein said first cam portion comprises a cam slot, wherein said closure member comprises a cam follower positioned within said cam slot, wherein said proximal drive portion comprises a proximal drive surface and a distal drive surface, and wherein said second cam portion comprises a drive member configured to engage said distal drive surface and move said firing member from said proximal position to said distal position when said trigger is moved through said second range of motion.

8. The surgical instrument of claim 7, wherein said drive member is configured to engage said proximal drive surface of said proximal drive portion when said trigger is returned through said second range of motion.

9. The surgical instrument of claim 7, wherein said drive member is not engaged with said distal drive surface when said trigger is moved through said first range of motion.

10. The surgical instrument of claim 7, wherein said cam slot comprises an acceleration portion corresponding to said first range of motion of said trigger and a dwell portion corresponding to said second range of motion of said trigger.

11. The surgical instrument of claim 10, wherein said cam follower is configured to enter said dwell portion when said drive member is engaged with distal drive surface.

12. A surgical instrument, comprising:
an end effector, comprising:
   a first jaw;
   a second jaw, wherein said first jaw is movable relative to said second jaw between an open position and a closed position; and
   at least one electrode;
a closure member operably coupled with said first jaw;
a firing member movable between a proximal position and a distal position, wherein said firing member comprises:
   a distal portion positionable within said end effector; and
   a proximal drive portion; and a handle comprising a trigger movable through a first range of motion and a second range of motion, said trigger comprising:
- a first cam portion operably engageable with said closure member, wherein the movement of said trigger through said first range of motion is configured to impart a closing motion to said closure member and move said first jaw between said open position and said closed position; and
- a second cam portion operably engageable with said proximal drive portion of said firing member, wherein the movement of said trigger through said second range of motion is configured to impart a firing motion to said firing member and move said firing member from said proximal position to said distal position, and wherein said closing motion is configured to pull said closure member proximally in order to close said first jaw, and wherein said firing motion is configured to push said firing member distally in order to advance said firing member within said end effector.

\* \* \* \* \*